United States Patent
Courtray

(10) Patent No.: US 6,298,714 B1
(45) Date of Patent: Oct. 9, 2001

(54) DEVICE FOR PERFORMING TESTS ON ABSORBENT SUBSTRATES

(76) Inventor: Franck Courtray, Centre Tertia ZI Douai-Dorignies, 710 rue J. Perrin, 59500 Douai (FR)

( * ) Notice: Subject to any disclaimer, the term of this patent is extended or adjusted under 35 U.S.C. 154(b) by 0 days.

(21) Appl. No.: 09/461,770

(22) Filed: Dec. 15, 1999

(30) Foreign Application Priority Data

Dec. 17, 1998 (FR) .................................. 98 16271

(51) Int. Cl.$^7$ ........................ G01N 25/56; G01N 15/08
(52) U.S. Cl. ........................................ 73/73; 73/38
(58) Field of Search .................... 73/73, 38, 76; 604/358, 378

(56) References Cited

U.S. PATENT DOCUMENTS

| | | |
|---|---|---|
| 4,041,737 | 8/1977 | Masci . |
| 4,332,175 * | 6/1982 | Krainski, Jr. ............................ 73/825 |
| 4,976,138 * | 12/1990 | Benninghoff et al. .................. 73/73 |
| 5,361,627 * | 11/1994 | Levesque ................................ 73/73 |
| 5,675,079 * | 10/1997 | Gilman et al. ....................... 73/118.1 |
| 5,990,377 * | 11/1999 | Chen et al. .......................... 604/381 |
| 6,085,579 * | 7/2000 | Herrlein .................................. 73/73 |

FOREIGN PATENT DOCUMENTS

| | | |
|---|---|---|
| 0 022 044 A1 | 1/1981 | (EP) . |
| 0 359 501 A2 | 3/1990 | (EP) . |
| 0 692 232 A1 | 1/1996 | (EP) . |
| 0 797 967 A1 | 10/1997 | (EP) . |
| 0 797 968 A1 | 10/1997 | (EP) . |
| 0 813 849 A1 | 12/1997 | (EP) . |

* cited by examiner

Primary Examiner—Hezron Williams
Assistant Examiner—Jay L. Politzer
(74) Attorney, Agent, or Firm—Miles & Stockbridge P.C.; John C. Kerins

(57) ABSTRACT

The invention relates to a device (1) for performing tests on absorbent substrates (2), particularly by applying at least one of the opposite sides (2A, 2B) of said substrate (2) to a receiving surface (3A, 7).

Figure 1:
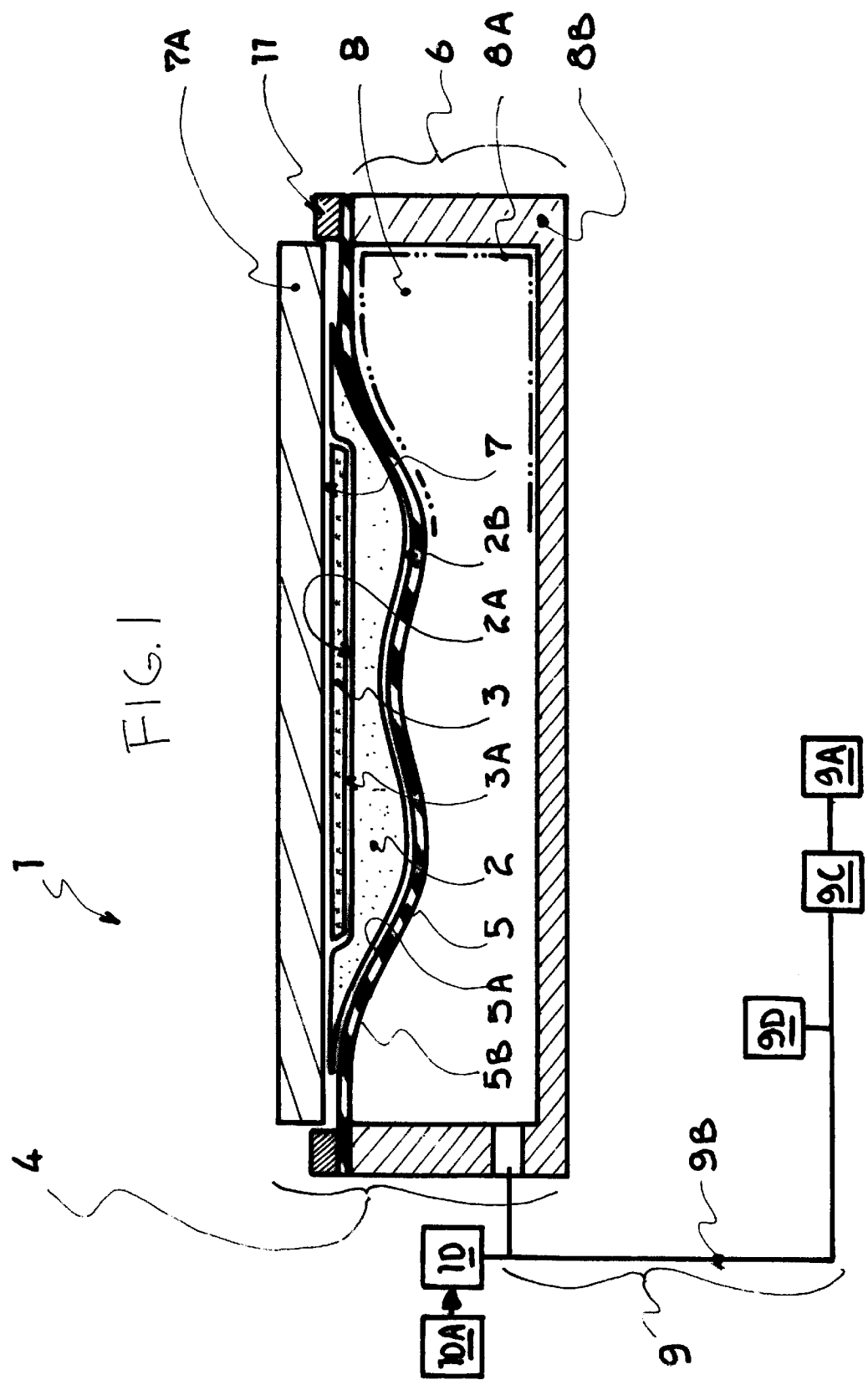
Figure 2:
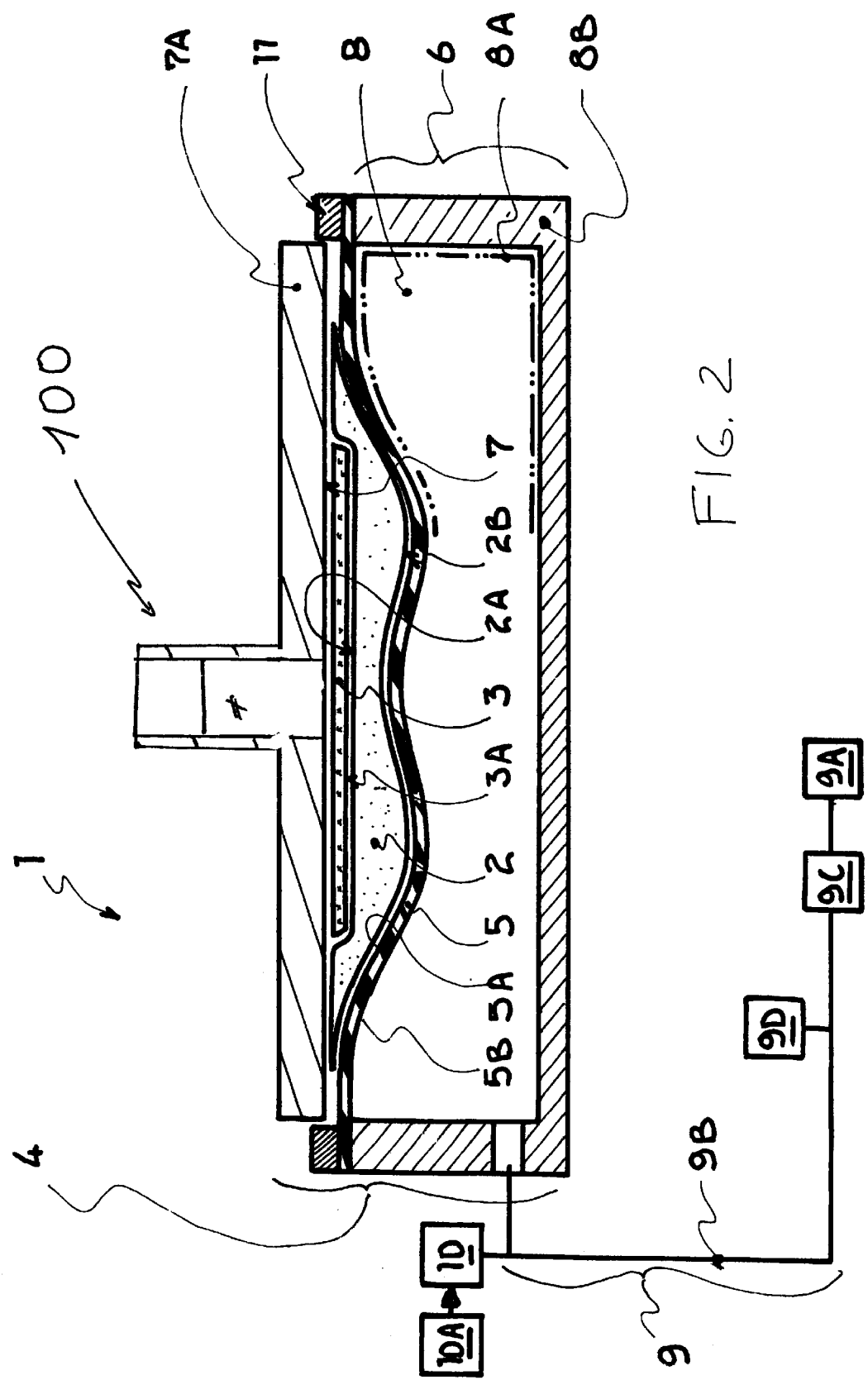

This device is characterized in that it comprises a means (4) whose function is to ensure the tight application of the substrate (2) to a receiving surface (3A, 7), i.e., a means capable of elastically deforming at least this substrate (2) so that it is tightly pressed against said receiving surface (3A, 7).

9 Claims, 2 Drawing Sheets

DEVICE FOR PERFORMING TESTS ON ABSORBENT SUBSTRATES

The invention relates to a device for performing tests on absorbent substrate.

The invention concerns a device for performing tests on absorbent substrates particularly by applying at least one so-called test element to a surface of this substrate.

The invention applies, advantageously though not exclusively, to a device for performing so-called "rewet" tests, on absorbent pads used in the making of hygiene products of the absorbent type, or on the absorbent products themselves.

Hygiene products of the absorbent type means products that comprise at least one pad of absorbent material, for example absorbent in capillary fashion, one surface of which is intended to be at least indirectly applied to a person's body in order to collect a fluid.

In terms of performance, absorbent products such as diapers for babies, products for incontinent persons or feminine hygiene products are evaluated based on two criteria:

capacity to absorb and retain the fluids emitted during use, which may be considered leak prevention, capacity to isolate the user from the fluids emitted, which can be expressed as moisture prevention.

The constant development of the markets for absorbent products requires manufacturers to continually measure the respective performance of their products based on these two criteria.

While consumer panels can provide relatively precise and reliable information on the rate of leaks, these studies, in order to be statistically valid, must be extensive and are therefore very costly.

But it is mostly because of the response times, which are always very long, that it was necessary to develop laboratory methods that were much faster and more economical.

Access to dummy systems such as the "lab service capability tester" and continuing studies of the correlations obtained between this system and consumer panels have allowed many manufacturers to quickly obtain precise and reliable information on the rate of leaks in their products.

By contrast, the measurement of moisture protection by panels is far more complex and far less reliable.

This is linked, for example, to the variability factors resulting from the individuals and the intrinsic characteristics of their skin.

Moreover, while the "leak" parameter is very pragmatic (leaks either do or do not exist), the same cannot be said for the evaluation of moisture, which is a parameter that is partially subjective (slightly moist, moist, very moist . . . how can this performance be objectively quantified?).

For many years, the evaluation of "moisture prevention" was performed in two different ways, i.e., in vivo and in the laboratory.

In the laboratory, tests were performed based on two measurement concepts:

the so-called "rewet" measurement, the measurement of surface moisture or contact moisture.

Tests performed in vivo directly involve the properties of the skin of the person wearing the product, but also the normal conditions for use of said products.

The results of tests performed in vivo, which should more accurately reflect the behavior of absorbent products than tests performed in the laboratory, have in fact proven to be subject to problems of interpretation involving a substantial population of the individuals tested.

Researchers attempted to find a solution that would make it possible to perform laboratory tests with a substantial correlation to tests performed in vivo.

Researchers worked to develop an element which, intended to be applied to the absorbent substrate to be tested, had properties comparable to those of people's skin.

Greatly improved test elements using, for example, collagen, were developed and are used today, both for "rewet" measurement and for measuring surface moisture or contact moisture.

As indicated above, the device of the invention relates advantageously, i.e., in a non-limiting way, to rewet measurement.

A rewet test means a test in which:

a sample absorbent pad receives a certain quantity of liquid, for a predetermined amount of time, the sample is subjected to a pressure, also predetermined, in order to ensure the diffusion and/or the distribution of the liquid, at least one element of absorbent material, of predetermined weight, is then applied to a surface of the sample and held against this surface for a predetermined amount of time and with a predetermined pressure, at the end of the application stage, each element of absorbent material is weighed in order to determine the total quantity of liquid collected.

There are many variants of this test, depending for example on the nature of the absorbent elements used, their dimensions and shapes, etc.

The inventor observed that the elements of absorbent material used were generally thin sheets of material, such as elements cut from sheets of filter paper, of collagen, and were applied to the samples to be tested by means of solid bodies.

Nowadays, hygiene products of the absorbent type usually have a structure that is non-uniform.

For example, they can have one of the following criteria:

a fluid-receiving surface that is anatomically conforming, and a thickness and/or a density that varies depending on the measuring point on the receiving surface.

On articles of this type, rewet tests conducted according to the techniques of the prior art are unreliable, i.e., not only do they give different results on identical articles, but also, they do not reveal the actual rewet indices of the articles tested.

One object of the invention is to obtain a device that, while being economical to produce, allows the effective application of absorbent test elements to absorbent articles whose structure is not uniform.

To this end, the subject of the invention is a device for performing tests on absorbent substrates, particularly by applying at least one of the opposite sides of said substrate to a receiving surface, this device being particularly characterized in that it comprises a means whose function is to ensure the tight application of the substrate to this receiving surface, i.e., a means capable of elastically deforming at least this substrate so that it is pressed tightly against said receiving surface, the tight application means comprising:

a thin wall made of elastically deformable material which, having a size substantially larger than the size of either of the opposite sides of the substrate to be tested, has two opposite sides of its own, including a so-called frontal side, intended to cooperate at least indirectly with one side of the substrate, and an opposite, so-called dorsal side, intended to receive actions for applying the frontal side to the substrate, a means for producing application actions against the dorsal side of the thin wall, a receiving surface oriented for receiving, at least indirectly, the substrate pressed against it under the action of the thin wall.

The invention will be clearly understood through the reading of the description below, given as a non-limiting example in reference to the attached drawing, which schematically represents:

FIG. 1: a device according to the invention seen in cross-section

FIG. 2: a variant.

Referring to the drawing, we see a device 1 for performing tests on absorbent substrates 2, particularly by applying at least one of the opposite sides 2A, 2B of said substrate 2 to a receiving surface 3A, 7, such as a surface 3A of at least one element 3, called a test element.

Advantageously, but in a non-limiting way, the device makes it possible to perform so-called rewet tests on such substrate.

The term absorbent substrates 2 designates, especially but not exclusively, the absorbent pads used in the making of hygiene products of the absorbent type, or the absorbent products themselves.

Such substrates 2 therefore comprise at least one pad of absorbent material, for example absorbent in capillary fashion, wherein a so-called receiving side is intended to be at least indirectly applied to a person's body (not represented) in order to collect a fluid.

According to the invention, the device 1 is remarkable in that it comprises a means 4 whose function is to ensure the tight application of the substrate 2 to a receiving surface 3A, 7, i.e. a means 4 capable of elastically deforming at least this substrate 2 so that it is pressed tightly against said receiving surface.

When a side 2A of the substrate 2 must be directly applied to a receiving surface 7, the tight application means 4 ensures the elastic deformation of said substrate 2 in order to effectively place the receiving surface 7 in contact with the side 2A of this substrate 2 in question.

When a side 2A of the substrate 2 must be applied against a receiving surface 3A such as a side 3A of a test element 3, the tight application means 4 ensures the elastic deformation of said substrate and, if necessary, of the test element 3, in order to effectively place the receiving surface 3A of this test element 3 in contact with the side 2A of this substrate 2 in question.

Remarkably, the tight application means 4 is capable of ensuring a uniform pressure for applying the absorbent substrate 2 to the receiving surface 3A, 7.

In particular, the device of the invention makes it possible, when an absorbent element 3 is used for a test, for it to be tightly applied to the side of the substrate tested, even when the area of the application of the element 3 has depressions, i.e., parts that are recessed due to the reduced thickness and/or local density of the substrate.

With the testing devices of the prior art, which used at least one solid rigid body for the application of each absorbent element to a side of a substrate to be tested, this result could not be obtained because said solid body would primarily only be pressed against the projecting parts of the side of the substrate, and only accidentally onto the areas recessed from these projecting parts.

Since the device of the invention comprises a means 4 capable of elastically deforming at least one of the pieces 2, 3, i.e., the substrate 2 and the test element 3, so that they are tightly pressed against one another by the sides 2A, 3A in contact, it therefore makes it possible to eliminate the drawbacks of the testing devices of the prior art.

In one remarkable embodiment, the tight application means 4 comprises:

a thin wall 5 of elastically deformable material which, having a size substantially larger than the size of either of the opposite sides 2A, 2B of the substrate 2 to be tested, has two opposite sides 5A, 5B of its own, including a so-called frontal side 5A, intended to cooperate at least indirectly with one side of the substrate 2, and an opposite, dorsal side 5B, intended to receive actions for applying the frontal side 5A to the substrate 2, a means 6 for producing application actions against the dorsal side of the thin wall 5, a receiving surface 7 oriented for receiving, at least indirectly, the substrate 2 pressed against it under the action of the thin wall 5.

In one embodiment, the device comprises:

a capacity 8 defined by a wall 8A at least locally constituted by the thin wall 5, a controlled means 9 for injecting a fluid under a predetermined pressure into this capacity 8, a controlled means 10 for emptying the capacity 8, a structure 11 for holding a surface 7 oriented so as to face the frontal side 5A of the thin wall 5 in order to receive, at least indirectly, the substrate 2 pressed against it during the action of the thin wall 5.

When a test element 3 is used, it is preferably placed against one 2A of the opposite sides 2A, 2B of the substrate 2 which must be applied to the receiving surface 7 held by the structure 11.

The controlled means 9 for injecting a fluid under pressure into the capacity 8 comprises:

a source 9A of fluid under pressure, a conduit 9B that connects the source 9A and the capacity 8, a controlled device 9C for controlling the passage of the fluid under pressure through the conduit 9B.

Preferably, the source of fluid under pressure is a source of gaseous fluid, such as air, and this source delivers the fluid under a predetermined, but adjustable, pressure.

Preferably, the controlled means 9 comprises a device 9D for displaying the pressure of the fluid under pressure.

Remarkably, the controlled means 10 for emptying the capacity 8 is controlled by a timing means 10A.

This way, the operator can define a time for the application under pressure of the substrate 2 and the absorbent element 3.

In one embodiment, the capacity 8 is constituted by the internal volume of a vessel 8B substantially produced by a rigid wall and locally by the thin wall 5.

For example, the vessel 8B has a substantially parallelipipedic rectangular shape.

According to one embodiment, the thin wall 5 consists in a membrane 5 tightly joined to the vessel 8B by its periphery.

According to another embodiment, the frontal side 5A of the thin wall 5 is constituted by one of the sides of a flexible bag housed in the vessel 8B (version not represented).

In one embodiment, the structure 11 for holding a surface 7 oriented so as to face the frontal side 5A of the thin wall 5 comprises:

a plate 7A of material having such a surface 7 oriented so as to face the frontal side 5A of the thin wall 5, a bracket 11 that holds the plate 7A and for this reason extends above the membrane 5 in order to hold said plate at a distance that substantially corresponds to the thickness of the substrate 2.

Advantageously, the bracket 11 is constituted by a frame that extends at the periphery of, and above, the thin wall 5.

Remarkably, the plate 7A of material is articulated on the bracket 11 between two positions, including
   a neutral position that allows access to the frontal side of the thin wall 5, particularly in order to put the substrate 2 in place or remove it, and
   an application position that guarantees the holding of the receiving surface 7 of this plate 7A so that it faces the frontal side 5A of the thin wall 5, in order to receive, at least indirectly, the substrate 2 pressed against it during the action of the thin wall 5.

In using the device of the invention, preferably, but in a non-limiting way, it is the so-called receiving surface of the substrate that, once fitted with at least one absorbent test element, is placed in contact with the plate of material 7A.

Remarkably, the plate of material 7A is made of a material that is transparent to at least a certain wave band.

For example, the plate of material 7A is made of a material that is transparent to light.

This technical characteristic makes it possible to observe the side of the substrate 2 and/or the test element 3 that is applied to the plate 7A.

The plate of material 7A can advantageously be curved and can even have a shape that approximates an individual's anatomy.

The vessel 8B and the thin wall 5 would quite clearly be adapted for receiving and being applied to the aforementioned curved surface.

In a variant of embodiment, the device can perform various tests for measuring absorption time with or without the maintenance of the hydrostatic pressure.

For this purpose, the plate 7A would be provided with at least one opening surmounted by a shaft 100 into which a liquid to be absorbed by the absorbent substrate is introduced.

Electrodes placed at the base of the shaft and at a sufficient distance from the absorbent substrate, several millimeters above the substrate, create an electrical contact as long as there is liquid in this shaft.

Using a computer, it is possible to perform multiple acquisitions automatically, for example in order to simulate multiple micturitions.

The so-called acquisition and/or rewet test is thus automated and high-performance as a result of the means implemented and explained above.

What is claimed is:

1. Device (1) for performing tests on absorbent substrates (2), particularly by applying at least one of the opposite sides (2A, 2B) of said substrate (2) to a receiving surface (3A, 7), this device being characterized in that it comprises a means (4) whose function is to ensure the tight application of the substrate (2) to this receiving surface (3A, 7), i.e., a means (4) capable of elastically deforming at least this substrate (2) so that it is tightly pressed against said receiving surface (3A, 7), the tight application means (4) comprising:
   a thin wall (5) of elastically deformable material which, having a size substantially larger than the size of either of the opposite sides (2A, 2B) of the substrate (2) to be tested, has two opposite sides (5A, 5B) of its own, including
     a so-called frontal side (5A), intended to cooperate at least indirectly with one side of the substrate (2), and
     an opposite, so-called dorsal side (5B), intended to receive actions for applying the frontal side (5A) to the substrate (2),
   a means (6) for producing application actions against the dorsal side of the thin wall (5),
   a receiving surface (7) oriented for receiving, at least indirectly, the substrate (2) pressed against it under the effect of the thin wall (5), and
   means for acquiring data pertaining to a characteristic of said absorbent structure to be tested.

2. Device according to claim 1 characterized in that the tight application means (4) is capable of ensuring a uniform pressure for applying the absorbent substrate (2) to the receiving surface (3A, 7).

3. Device according to claim 2, characterized in that:
   a capacity (8) defined by a wall (8A) at least locally constituted by the thin wall (5),
   a controlled means (9) for injecting a fluid under a predetermined pressure into this capacity (8),
   a controlled means (10) for emptying the capacity (8),
   a structure (11) for holding a surface (7) oriented so as to face the frontal side (5A) of the thin wall (5) in order to receive, at least indirectly, the substrate (2) pressed against it during the action of the thin wall (5).

4. Device (1) for performing tests on absorbent substrates (2), particularly by applying at least one of the opposite sides (2A, 2B) of said substrate (2) to a receiving surface (3A, 7), this device being characterized in that it comprises a means (4) whose function is to ensure the tight application of the substrate (2) to this receiving surface (3A, 7), i.e., a means (4) capable of elastically deforming at least this substrate (2) so that it is tightly pressed against said receiving surface (3A, 7), the tight application means (4) comprising:
   a thin wall (5) of elastically deformable material which, having a size substantially larger than the size of either of the opposite sides (2A, 2B) of the substrate (2) to be tested, has two opposite sides (5A, 5B) of its own, including
     a so-called frontal side (5A), intended to cooperate at least indirectly with one side of the substrate (2), and
     an opposite, so-called dorsal side (5B), intended to receive actions for applying the frontal side (5A) to the substrate (2),
   a means (6) for producing application actions against the dorsal side of the thin wall (5),
   a receiving surface (7) oriented for receiving, at least indirectly, the substrate (2) pressed against it under the effect of the thin wall (5),
   wherein said tight application means (4) is capable of ensuring a uniform pressure for applying the absorbent substrate (2) to the receiving surface (3A, 7),
   the device further comprising:
     a capacity (8) defined by a wall (8A) at least locally constituted by the thin wall (5),
     a controlled means (9) for injecting a fluid under a predetermined pressure into this capacity (8),
     a controlled means (10) for emptying the capacity (8),
     a structure (11) for holding a surface (7) oriented so as to face the frontal side (5A) of the thin wall (5) in order to receive, at least indirectly, the substrate (2) pressed against it during the action of the thin wall (5), and wherein
     the controlled means (9) for injecting a fluid under pressure into the capacity (8) comprises:
       a source (9A) of fluid under pressure, a conduit (9B) that connects the source (9A) and the capacity (8), a controlled device (9C) for controlling the passage of the fluid under pressure through the conduit (9B).

5. Device according to claim 4, characterized in that the controlled means (10) for emptying the capacity (8) is controlled by a timing means (10A).

6. Device according to any of claims 3 characterized in that the capacity (8) is constituted by the internal volume of a vessel (8B) substantially produced by a rigid wall (8A) and locally by the thin wall (5).

7. Device according to claim 6, characterized in that the thin wall (5) consists in a membrane (5) tightly joined to the vessel (8B) by its periphery.

8. Device according to any of claims 3 characterized in that the structure (11) for holding a surface (7) oriented so as to face the frontal side (5A) of the thin wall (5) comprises:

a plate (7A) of material having such a surface (7) oriented so as to face the frontal side (5A) of the thin wall (5), a bracket (11) that holds the plate (7A) and for this reason extends above the membrane (5) in order to hold said plate at a distance substantially corresponding to the thickness of the absorbent substrate (2).

9. Device according to claim 8, characterized in that the plate (7A) of material is articulated on the bracket (11) between two positions, including:

a neutral position that allows access to the frontal side of the thin wall (5), particularly in order to put the substrate (2) in place or remove it, and an application position that guarantees the holding of the receiving surface (7) of this plate (7A) so that it faces the frontal side (5A) of the thin wall (5) in order to receive, at least indirectly, the substrate (2) pressed against it during the action of the thin wall (5).

* * * * *

UNITED STATES PATENT AND TRADEMARK OFFICE
CERTIFICATE OF CORRECTION

PATENT NO. : 6,298,714 B1
DATED : October 9, 2001
INVENTOR(S) : Franck Courtray

It is certified that error appears in the above-identified patent and that said Letters Patent is hereby corrected as shown below:

<u>Column 7,</u>
Lines 9 and 16, "any of claims" should be changed to -- claim --.

<u>Column 8,</u>
Line 13, "(SA)" should be changed to -- (5A) --.

Signed and Sealed this

Twenty-eighth Day of May, 2002

Attest:

JAMES E. ROGAN
*Attesting Officer*     *Director of the United States Patent and Trademark Office*